(12) United States Patent
Hecker et al.

(10) Patent No.: US 9,918,642 B2
(45) Date of Patent: Mar. 20, 2018

(54) PRESSURE GAUGE

(71) Applicant: Fibragg Diagnostics GmbH, Frankfurt am Main (DE)

(72) Inventors: Raoul Hecker, Frankfurt am Main (DE); Thomas Barz, Schwedt (DE); Markus Melloh, Winterthur (CH)

(73) Assignee: Fibragg Diagnostics GmbH, Frankfurt am Main (DE)

( * ) Notice: Subject to any disclaimer, the term of this patent is extended or adjusted under 35 U.S.C. 154(b) by 0 days.

(21) Appl. No.: 15/030,481

(22) PCT Filed: Oct. 27, 2014

(86) PCT No.: PCT/EP2014/073030
§ 371 (c)(1),
(2) Date: Apr. 19, 2016

(87) PCT Pub. No.: WO2015/059311
PCT Pub. Date: Apr. 30, 2015

(65) Prior Publication Data
US 2016/0262627 A1 Sep. 15, 2016

(30) Foreign Application Priority Data

Oct. 25, 2013 (DE) .......................... 10 2013 111 817
Feb. 28, 2014 (DE) .......................... 20 2014 100 938

(51) Int. Cl.
*A61B 5/00* (2006.01)
*G01L 9/08* (2006.01)
(Continued)

(52) U.S. Cl.
CPC ........ *A61B 5/0084* (2013.01); *A61B 5/02154* (2013.01); *A61B 5/08* (2013.01);
(Continued)

(58) Field of Classification Search
None
See application file for complete search history.

(56) References Cited

U.S. PATENT DOCUMENTS

2004/0067000 A1   4/2004   Bates et al.
2008/0021289 A1   1/2008   Zhang et al.
(Continued)

FOREIGN PATENT DOCUMENTS

DE   10 2008 026 898 A1   12/2009
EP            1 154 269 A2   11/2001
(Continued)

OTHER PUBLICATIONS

International Search Report of PCT/EP2014/073030, dated Mar. 11, 2015.
(Continued)

*Primary Examiner* — Ankit D Tejani
(74) *Attorney, Agent, or Firm* — Collard & Roe, P.C.

(57) ABSTRACT

The invention relates to a pressure measuring device (1) for measuring pressure in a biological system, comprising a flexibly or resiliently designed measuring cell holder (3), wherein, in the measuring cell holder (3), there are at least two FBG sensors (4) which are arranged at a distance from one another. The measuring cell holder (3) can comprise a plurality of layers (5, 6) into which the FBG sensors (4) can be integrated.

18 Claims, 10 Drawing Sheets

Figure 1:
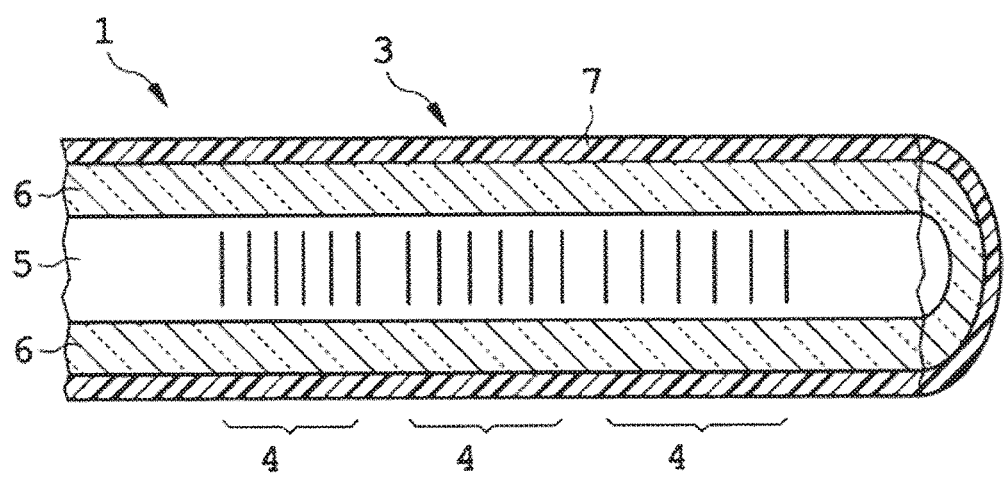

(51) Int. Cl.

| | |
|---|---|
| *A61B 5/0215* | (2006.01) |
| *G01L 9/00* | (2006.01) |
| *G01L 11/02* | (2006.01) |
| *G01L 1/24* | (2006.01) |
| *A61B 5/08* | (2006.01) |
| *A61B 5/20* | (2006.01) |
| *A61B 5/03* | (2006.01) |
| *A61B 17/00* | (2006.01) |
| *A61B 90/00* | (2016.01) |
| *A61B 34/20* | (2016.01) |
| *A61B 90/30* | (2016.01) |

(52) U.S. Cl.
CPC ............ *A61B 5/205* (2013.01); *A61B 5/6852* (2013.01); *A61B 90/06* (2016.02); *G01L 1/246* (2013.01); *G01L 9/0032* (2013.01); *G01L 9/08* (2013.01); *G01L 11/025* (2013.01); *A61B 5/02158* (2013.01); *A61B 5/03* (2013.01); *A61B 17/00234* (2013.01); *A61B 2017/0011* (2013.01); *A61B 2034/2061* (2016.02); *A61B 2090/064* (2016.02); *A61B 2090/065* (2016.02); *A61B 2090/306* (2016.02); *A61B 2560/0223* (2013.01); *A61B 2562/0233* (2013.01); *A61B 2562/0247* (2013.01); *A61B 2562/0266* (2013.01); *A61B 2562/228* (2013.01)

(56) References Cited

U.S. PATENT DOCUMENTS

| | | |
|---|---|---|
| 2008/0294144 A1 | 11/2008 | Leo et al. |
| 2012/0220879 A1 | 8/2012 | Fandrey et al. |

FOREIGN PATENT DOCUMENTS

| | | |
|---|---|---|
| EP | 2 491 883 A1 | 8/2012 |
| WO | 99/58059 A1 | 11/1999 |
| WO | 2009/146947 A1 | 12/2009 |

OTHER PUBLICATIONS

Esashi, Masayoshi [et al.], "Fabrication of Catheter-Tip and Sidewall Miniature Pressure Sensors," in: IEEE Transactions on electron devices, vol. 29, No. 1 Jan. 1982, pp. 57-63.

Guan, Bai-Ou [et al.], "Discrimination between strain and temperature with a single fiber bragg grating," in: Microwave and optical technology letters, vol. 33, No. 3, May 5, 2002, pp. 200-202.

Medical Measurement Systems b.v., "Solar GI HRM Fortschrittliche and kosteneffiziente High-Resolution-Manometrie," (Solar GI HRM Advanced and Cost-efficient High Resolution Manometry) 2012, Enschede Netherlands. pp. 1-6 (with English translation—total of 12 pages).

Voigt, Sebastian [et al.], "Investigations on pressure sensors for medical applications based on fiber bragg gratings," in: Proc. of the 17th Int. Conf. on Solid-State Sensors, Actuators and Microsystems, Jun. 16-20, 2013 Barcelona, Spain, pp. 78-81.

PRESSURE GAUGE

CROSS REFERENCE TO RELATED APPLICATIONS

This application is the National Stage of PCT/EP2014/073030 filed on Oct. 27, 2014, which claims priority under 35 U.S.C. § 119 of German Application No. 10 2013 111 817.8 filed on Oct. 25, 2013 and German Application No. 20 2014 100 938.8 filed on Feb. 28, 2014, the disclosures of which are incorporated by reference. The international application under PCT article 21(2) was not published in English.

The invention relates to a pressure measuring device for measuring pressure in a biological system, comprising a flexibly or resiliently designed measuring cell holder.

Catheter-based systems are known which are used in diagnostic and therapeutic applications. Catheter-based optical systems conventionally comprise a console which is for example portable, a mountable repository or a base station. An optical fibre probe, a camera or a catheter is connected to the console, sometimes also in a contactless manner, for example by means of electromagnetic waves.

The catheter is conventionally connected to the console by a connection adapter. The catheter is often only intended for a single use. Therefore the catheter must be removed after it has been used. Even if the catheter is not disposable, it must be removed for cleaning or sterilisation between the individual phases of use.

A likewise catheter-based measurement, which is manometric rather than imaging, is used to determine functional disorders for example in organs such as the oesophagus and the intestines. In this case, a pressure measurement is carried out in the organ and compared with a standard reference pressure, wherein conclusions can be drawn about possible functional disorders.

In perfusion manometry, a single-lumen or multi-lumen catheter is introduced into the oesophagus, wherein liquid flows through the channels of the catheter at as constant a flow rate as possible. Pressure fluctuations in the oesophagus can be detected by changes in the operating pressure.

Furthermore, the use of a microelectronic sensor is known, which sensor can be integrated for example in a catheter and is used to measure temperature or pressure. Temperature sensors generally use integrated doped resistors or diodes based on semiconductor substrates. The electrical properties of said components have a well-defined temperature dependency, which is exploited for the function thereof as a sensor. However, up to now, microelectronic pressure sensors have been used exclusively for hydrostatic pressure measurement, for example as a probe for measuring intracranial pressure.

Furthermore, it is possible to carry out a pneumatic pressure measurement using an intraventricular, subdural, intraparenchymal or epidural probe. The gas-filled chamber system used in this context is a hollow body made of plastics material which is connected to a pressure sensor by a tube. The pressure sensor is located, together with the measurement electronics and a device for filling the chamber system, in an ICP (intracranial pressure) monitor. To measure cerebral pressure, the gas-filled chamber system is placed in the ventricle or in the parenchyma. To measure epidural pressure/cerebral pressure, the chamber system is placed on the patient's dura mater. The intracranial pressure is transmitted via the thin wall of the chamber system to the air in the chamber system and converted into electrical signals by the pressure sensor.

In the prior art, tip sensors are also known, which consist of a catheter comprising a sensor element at the tip thereof. The actual pressure measuring plate of the sensor element comprises a fully or partially closed Wheatstone bridge. The bridge circuit is supplied with constant current by means of a wire line located in the catheter. If the pressure measuring plate is subjected to pressure, this leads to a change in the bridge output voltage as a result of the mechanical stress in the plate and the piezoresistive effect. The sensor is used for example in neurosurgical applications. They are subject to restrictions as a result of the very bulky construction, which is determined by the dimensions of the available piezo sensors.

Furthermore, devices are known by means of which for example a pressure in the oesophagus can be measured. In this case, a Bragg grating is integrated in a light guide. Various methods for producing such Bragg gratings (also known as fibre Bragg gratings) are known. For example, femtosecond lasers are used, by means of which the grating structures are introduced into the fibre core point by point. In this method, it is not necessary to remove the fibre coating. By contrast therewith, in the case of UV exposure with a phase mask or an excimer laser, the fibre coating must be removed point by point. The repeated application of the fibre coating after the exposure results in a point which is easy to break mechanically. Preferably therefore, the UV exposure is carried out directly at the fibre drawing tower before the coating is applied. When using UV light sources, it is additionally necessary to dope the fibre core with germanium. The known devices for measuring pressure in the oesophagus sometimes comprise a Bragg grating which is coupled with a movable wall portion. In addition, rigid fasteners are attached to the light guide at the side of the Bragg grating. By means of pressure acting on the movable wall portion, the movable wall portion moves towards the Bragg grating and in turn exerts a force on said grating so that the light guide is moved into a clearance delimited by the movable wall portions and the rigid fasteners. This movement or extension of the light guide results in an optical response by the Bragg grating. In the case of the known device, it is disadvantageous that the manufacture is very complex and costly. Due to the components arranged around the Bragg grating, the device has a very large diameter, which greatly restricts the use thereof. Furthermore, the device cannot be heat-sterilised, since the light guides are fixed to the movable wall portions and the rigid fasteners by bonding means. Due to the effect of temperature or other physical or chemical measures, the light guide can become detached from the bonding means, which in turn leads to irreparable damage and ultimately to a loss of function of the device.

In the case of the known pressure measuring devices, it is particularly disadvantageous that the pressure measurement takes place at only one point, and thus no spatially continuous measurement is possible. Furthermore, the known pressure measuring devices often cannot be sterilised, but rather are provided to be disposable, since they are difficult or impossible to clean, and this in turn is associated with high costs. A further disadvantage is that the pressure measuring devices cannot be used universally. In clinical use, constructions comprising metal components are also subject to considerable restrictions due to the fact that they exhibit electrical induction in magnetic resonance imaging (MRI) and thus disrupt the MRI scan and additionally develop electrical current, dislocation and heat in the biological system being studied. Diagnostic imaging methods based on X-rays, for example CT scans, can also be disrupted by metal components. Pressure measuring devices, which up to now have managed without metal components (for example pneumatic devices), in turn have the disadvantage that the shape thereof can often only be speculated by the examiner in clinical use, as a result of bends in the introduced organism.

The invention addresses the problem of providing a pressure measuring device which does not have the disadvantages and shortcomings of the known pressure measuring devices.

According to the invention, this problem is solved by a pressure measuring device for measuring pressure in a biological system, comprising a flexibly or resiliently designed measuring cell holder, wherein, in the measuring cell holder, there are at least two fibre Bragg grating sensors which are arranged at a distance from one another. Within the meaning of the invention, the fibre Bragg grating sensors can also be referred to as measuring cells. The pressure measuring device is designed to be flexible or resilient, in particular radially extensible or compressible, so that a radially acting force leads to a deformation of the measuring cell holder. It is known to a person skilled in the art that the original shape of the measuring cell holder can be achieved again when the acting force ceases, and thus the measuring cell holder is resilient or plastic. However, it can also be advantageous for the original shape not to be assumed again when the force effect ceases, and thus the measuring cell holder is flexible. The resilient or flexible design of the measuring cell holder can be affected by the material selected for the measuring cell holder, wherein a person skilled in the art knows that even a hard material can be elastically deformed by an appropriate force effect. By means of the resilient or flexible design of the measuring cell holder, it is achieved that external force effects bring about a radial extension or compression and thus a deformation of the measuring cell holder. By means of the device according to the invention, it is advantageously possible to capture pressure measurement results over a course of time, wherein, in addition, a change in location of the measuring cell holder or the biological system (in particular of a patient) can take place (for example sitting/lying down/standing, prone/supine position, or specific movements and loads).

The measuring cells are arranged at a distance from one another in the measuring cell holder. Even when the force effect on the measuring cell holder is low, it brings about a deformation of the measuring cell holder and thus an extension of the measuring cells. The acting force can thus be captured as a pressure by the measuring cells. Due to the fact that the measuring cells are arranged at a distance from one another, a plurality of, optionally different pressures can be measured. As a result, it is possible to carry out a spatially/temporally continuous pressure measurement in a biological system. However, it can also be advantageous for a measuring cell to capture pressures at two or more different measuring points in the biological system. The pressure measuring device can be guided from the first to the second measuring point for example by a shift in position, and can measure a first pressure at the first measuring point, and a second pressure at the second measuring point. This offers surprising advantages, since one of the measured pressures can be taken as a reference value. Measurement artefacts can thus be taken into consideration when measuring pressure and eliminated by means of the reference value.

It can also be advantageous for the pressure measuring device to determine pressures at a measuring point in a temporal sequence, i.e. a measuring cell can capture in particular at least two pressures at a measuring point in a temporal sequence, wherein the second measuring cell is used as a reference measuring cell.

Furthermore, the measuring cells can measure pressures one after the other or at the same time. This can be advantageous in particular when more than two, preferably more than five, particularly preferably more than ten measuring cells are at a distance from one another in the measuring cell holder. As a result, pressures can be determined over a great length of the measuring cell holder. It is possible for the measuring cells to capture the pressures at the same time or one after the other.

Advantageously, the pressure measuring device can be introduced (inserted) into a biological system easily and safely by an axially acting propulsive force or compressive load, wherein the pressure measuring device is subject to substantially no axial compression. It has become apparent that the pressure measuring device is advantageously subject to no significant compression, and the insignificant compression of the pressure measuring device after the load relief, for example after the acting propulsive force ceases, is offset. The pressure measuring device, within the meaning of the invention, with respect to an axially acting propulsive force or compressive load, can thus in particular be referred to as substantially propulsion stable. The length of the pressure measuring device is substantially unchanged by the axially acting forces. This offers the advantage that the pressure measuring device can easily be introduced into a biological system and is easy to guide or manoeuvre therein, and in addition, the risk of injury to the biological system is reduced.

Also by means of an axially acting tensile load, substantially no deformation of the pressure measuring device is brought about, and therefore it is also possible to easily and safely remove the pressure measuring device from the biological system.

Within the meaning of the invention, a biological system refers in particular to a living creature, in particular a human being, a farm animal or a domestic animal. Farm animals preferably include all breeds of domestic animals used in agriculture, regardless of whether said farm animals are used for nutritional purposes or as pack or draught animals. Furthermore, farm animals include in particular all types and breeds of animals which have been domesticated primarily for the supply of wool, and likewise types of animals and breeds of domestic animals which humans consider useful in other ways. The term "domestic animals" describes in particular all domesticated types and breeds of animals. The pressure measuring device according to the invention can be used for measuring pressure universally in biological systems.

The pressure measuring device is in particular in the form of a thread-shaped or tubular entity, the measuring cell holder advantageously comprising a first and a second end. The first end of the pressure measuring device can be referred to as the end which is close to the evaluation unit. The second end of the measuring cell holder, i.e. the end which can be introduced into a biological system, is referred to within the meaning of the invention as the end which is remote from the evaluation unit. In one embodiment of the invention, the end which is remote from the evaluation unit can comprise an atraumatic tip or guiding structure. The guiding structure can be for example a fixed or removable and/or insertable guide wire or a structure which is suitable for facilitating introduction into outgoing or branched biological structures.

The atraumatic tip is preferably produced from a plastics material of a type such that the biological system is not injured when the pressure measuring device is introduced. Preferred plastics materials are polyoxymethylene, polyurethane and/or polyamide. In experiments, it has been found that the tip does not cause any injury to the biological system when it is introduced into the biological system. In order to additionally improve the introduction, in a preferred embodiment, the tip can comprise a bulge or a rounding. Also for preferred applications, for example of a pressure measurement by means of the pressure measuring device according to the invention, in coronary vessels, a special extension of the pressure measuring device made of a flexible material can be present, which for example is initially straight due to an inner splinting (stylet), and can then assume a bent shape when the splinting is pulled out.

The introduction of the pressure measuring device preferably takes place via punctures into the biological system using conventional hollow needles (trocar). When puncturing into arterial systems at relatively high pressure, said hollow needles can be combined with transfer tube systems. Said needles either remain at the puncture site or are pulled back and replaced with an internal tube. Equally, however, the pressure measuring device can advantageously also be introduced via naturally occurring orifices in the biological system or by means of surgery.

The pressure measuring device is subsequently preferably taken out again. Equally however, it can also remain in the biological system temporarily or even permanently. Equally, the pressure measuring device can also be introduced by means of surgery and optionally subsequently taken out again, in some circumstances also by further surgery.

At the end which is close to the evaluation unit, an electronic supply and evaluation unit, a data processing unit and/or an open and closed-loop control unit, and the optionally required energy and communication supplies can be connected. As a result, it is possible to carry out efficient detections and calculations, with minimal errors, of the pressure or pressures and/or differences in pressure and/or catheter bends and/or temperatures.

In a preferred embodiment, the measuring cell holder is an optical waveguide, in particular a monomode fibre. The measuring cell holder can also comprise an electrically conductive cable. The optical waveguide is preferably a polymer optical fibre or a glass fibre. Optical waveguides transmit light or light signals over long distances. The optical waveguide according to the invention can be produced from quartz, glass or a plastics material, in particular from a polymer optical fibre.

The optical waveguide can comprise a central region, which is also referred to as the core, wherein an optical waveguide can also comprise a plurality of cores. The core preferably consists of a material having a different, for example higher, index of refraction than the cladding surrounding the central region or core which is likewise produced from an optically conductive material. At the interfaces between the core and the cladding of the optical waveguide, optical reflections take place so that the light beam is conducted around each bend in a predominantly loss-free manner. The cladding is the likewise optically transparent material at which the reflection preferably takes place. The cladding can consist of a material which for example has a lower index of refraction than the core. The cladding and the core preferably consist of dielectric materials which are not metal and are non-conductive. A pressure measuring device is also provided which comprises a plurality of layers, i.e. cladding layers. In this case, the different layers can consist of different materials and thus can also have different material properties. This can be advantageous for example in specific applications in which a certain degree of flexibility of the pressure measuring device is required. Furthermore, the flexibility of the pressure measuring device is also changed by the introduction of a stiffening means therein. The stiffening means can be designed for example as a guide means and can be introduced into a lumen, in particular a working channel, of the pressure measuring device. The stiffening means can have different levels of stiffness in this regard, so that the stiffening means can be selected according to the desired flexibility of the pressure measuring device. In addition, the sensitivity of the pressure measuring device can be increased, reduced, adjusted and/or otherwise adapted by the combination of various cladding layer properties or various cladding layers having different properties in each case.

In one embodiment of the invention, it is provided that the measuring cell holder comprises an outer protective layer which consists of a biocompatible material. In this case, said layer can be for example a plastics coating which is applied as mechanical protection to the surface of the cladding material and is designed to be biocompatible. The protective layer can be extruded for example around the cladding layer. For the advantageous embodiment, plastics materials can be used from the group comprising modified natural substances, synthetic plastics materials (polycondensates, polymers, polyadducts), thermosetting materials, and/or unsaturated polyester resins, including cellulose nitrate, cellulose acetate, cellulose mixed ester, cellulose ester, polyamide, polycarbonate, polyester, polyphenylene oxide, polysulfone, polyvinyl acetal, polyethylene, polypropylene, poly(1-butene), poly(4-methyl-1-pentene), ionomers, polyvinyl chloride, polyvinylidene chloride, polymethyl methacrylate, polyacrylonitrile, polystyrene, polyoxymethylene, fluorine-based plastics materials, polyvinyl alcohol, polyvinyl acetate, poly(p-xylylene), linear polyurethanes, chlorinated polyether, casein plastics materials, cross-linked polyurethane, silicone, polyimide and/or polybenzimidazol. Duromers, elastomers or thermoplastics are particularly preferred. Experiments have shown that a protective layer or protective envelope made of a thermoplastic polymer is particularly advantageous because firstly, the measuring cell holders are well protected, and secondly, acting forces, in particular pressures to be measured, are transmitted to the measuring cell holders or the measuring cells with substantially no loss. The advantages of the preferred plastics materials are the biocompatibility thereof and the high flexibility thereof when extruded. In addition, the pressure measuring devices produced therefrom can be sterilised. Thermoplastics are preferably selected from the group comprising acrylonitrile butadiene styrene (ABS), polyamides (PA), polylactate (PLA), polymethyl methacrylate (PMMA), polycarbonate (PC), polyethylene terephthalate (PET), polyolefins, in particular polyethylene (PE) and polypropylene (PP), polystyrene (PS), polyetheretherketone (PEEK), polyacetals, polyvinyl chloride (PVC), cellulose acetate butyrate (CAB), cellulose acetate propionate (CAP) and styrene acrylonitrile (SAN). Surprisingly, poly(organo)siloxanes can also be used.

If the optical waveguide breaks, the protective layer can prevent individual parts from breaking off from the pressure measuring device and for example leading to injuries in the biological system or accidentally being left in said system. Within the meaning of the invention, biocompatible refers in particular to a material of the measuring cell holder which, when in direct contact with the biological system, has no disadvantageous effect on the metabolism or biological functionality thereof.

The pressure measuring device according to the invention comprises fibre Bragg grating sensors (FBG sensors). In one embodiment of the invention, it can be provided that the measuring cell holder comprises a piezoelectric sensor in the first and/or second layer, so that in addition to the FBG sensors, there are piezoelectric sensors for measuring pressure in the pressure measuring device. In another embodiment of the pressure measuring device, there are FBG sensors and piezoelectric sensors in the measuring cell holder, the sensors being present in the same layer or in different layers of the measuring cell holder. FBG sensors or piezoelectric sensors are referred to within the meaning of the invention as measuring cells. FBG sensors are optical sensors which reflect a specific light wavelength which is contingent on the grating structure in each case and is changed by temperature and/or mechanical forces. A mechanical extension or compression of the measuring cell holder, in particular of the optical waveguide, leads to an extension or compression of the grating and, as a result of the photoelastic effect, to a change in the wavelength which is reflected by each FBG sensor. FBG sensors detect in particular radial extensions of the measuring cell holder. In experiments, it has been found that the measuring cell holder according to the invention has a substantially constant length and is substantially not compressed by an axially acting force effect. The measuring cells according to the invention, in particular the FBG sensors, thus ultimately predominantly detect extensions due to forces acting radially on the measuring cell holder.

FBG sensors can be produced according to methods which are known in the prior art. If light having a broad spectrum is coupled with FBG sensors in an optical waveguide, a narrow-band spectral reflection takes place at the FBG structures. The reflection wavelength or Bragg wavelength depends in this case on the grating period of the respective FBG sensors. FBG sensors can preferably be in the core of the optical waveguide, and also in the cladding, i.e. introduced into different layers in the pressure measuring device.

Thus an FBG sensor advantageously reflects a specific light frequency, whereas all other frequencies are transmitted in such a way that they are virtually unchanged. Since the Bragg wavelength is a function of the distance between the gratings, FBG sensors can be used with various Bragg wavelengths in a measuring cell holder, in particular an optical waveguide, so that various wavelengths of the light are reflected. A change in the temperature and/or extension affects both the effective index of refraction and the grating period of an FBG sensor and advantageously lead to a change in the reflected wavelength. Since an FBG sensor reacts both to extension and to temperature, advantageously both influencing factors can be taken into consideration. In this case, it can be provided that the measuring cells of the pressure measuring device are calibrated to the temperature and pressure behaviour thereof either separately according to the pressure measuring device or according to the type of series production.

As a result of the low or negligible line losses and also as a result of the cost-effectiveness, a large distance, for example of 1 m or even 5 m or even more than 10 m can be achieved by a long wire between the measuring cells and the end of the pressure measuring device which is close to the evaluation unit, which offers advantages in particular in terms of handling.

To measure temperature and/or to quantitatively detect the effects of temperature on the shift measured in the Bragg wavelength, it may be preferable for at least one fibre Bragg grating sensor to be present as a reference measuring cell in an axially inflexible region of the measuring cell holder. Said measuring cell, in particular an FBG sensor, can be used as a reference measuring cell for the effect of temperature on the FBG sensor, and/or on the pressure measuring device. In order to design a region of the measuring cell holder to be inflexible, it can be advantageous to coat the measuring cell holder, in particular the optical waveguide, in the region of the reference measuring cell with a radially inflexible layer, for example with a metal layer or even a hard plastics material. By means of the coating, it can be ensured that the FBG sensor is not subjected to any bending, tension, compressive or torsional forces, and thus merely the temperature has an effect on the light reflection of the FBG sensor. The effect of the temperature on the reflection of the FBG sensor can be offset by the effect of a pressure on an FBG sensor which is at a distance from the reference measuring cell so that, as a result, merely the effect of the pressure on the reflection is detected. Equally, the effect of temperature can be eliminated up to a point by analytical methods.

Advantageously, a plurality of fibre Bragg grating sensors which are present in the measuring cell holder can have different resonance properties, i.e. a plurality of FBG sensors having different Bragg wavelengths can be introduced into an optical waveguide in series. The respective FBG sensors can then be activated or analysed individually by means of a wavelength division multiplexing (WDM) method. This spectral analysis can be carried out for example by means of a spectrometer, a spectral filter or an adjustable Fabry-Pérot étalon. An alternative system for reading out the FBG sensors is the use of a narrow-band adjustable laser as a light source and a photodiode as a detector. Even in the case of losses or attenuations in light intensity in the optical waveguide, FBG sensors provide precise results. Even bends in the optical waveguide as a result of the structure of the biological system or as a result of the type of application only disrupt the transmission of information from the FBG sensors to an insignificant extent. The number and position of the FBG sensors can preferably be designed for the measuring object or the biological system in such a way that an optimum detection of the spatial pressure distribution can take place at the measuring object, and thus possible sources of disruption can also be compensated.

In a preferred embodiment, the size of the respective FBG sensors inside the optical waveguide, i.e. the length thereof inside the optical waveguide, can be the same in each case, or the lengths can also vary, according to the application. Thus for example the FBG sensor which is furthest away from the examiner can also have a special configuration at the second end of the pressure measuring device. In terms of production, the reflectivity of the individual FBG sensors can in particular be designed and produced in such a way that the amplitude of the reflected signals of the FBG sensors at the output of the pressure measuring device is approximately equal. In an additional advantageous embodiment, the length of the respective FBG sensors can be adapted to the damping properties of each optical waveguide material, for example in inverse proportion. In one embodiment of the invention, the FBG sensors can be configured as a continuous grating, i.e. the distances between FBG sensors are very small and are virtually zero. As a result, it is possible to measure the run time or various reflection peaks, which in turn makes it possible to draw conclusions about the pressures. A change in frequency of the grating, for example chirped structures, of the FBG sensors can also be advantageous. In an additional embodiment, at least two measuring cell holders are integrated in a protective envelope or a cladding, the FBG sensors of the measuring cell holder being arranged so as to overlap one another, and thus a runtime measurement is also made possible. In such an embodiment, the Bragg wavelengths of the FBG sensors can be coordinated and may for example overlap.

One advantage of FBG sensors is that they are not susceptible to electromagnetic disruptions and are not subject to induction due to electromagnetic fields. They are also predominantly transparent for rays. As a result, pressure measuring devices comprising FBG sensors as measuring cells can easily be combined in the application with other diagnostic or therapeutic devices (magnetic resonance scanners, X-ray source assemblies, nuclear magnetic resonance spectroscopes, electron/particle beams etc.), which in turn increases the complexity of the possible diagnostics or therapies to a surprising extent.

When introducing a plurality of FBG sensors into an optical waveguide, it should advantageously be noted that the FBG sensors used differ from one another to a sufficient extent to prevent crosstalk of the reflection maxima of the Bragg wavelengths of extended or compressed gratings with other introduced FBG sensors during evaluation.

Since the available light frequency bands are restricted by the optical properties of the optical waveguide, the preferred FBG sensors can be used in a selectively economic manner for the application planned in each case. In biological systems, initially only low, optionally negligible differences in temperature are to be expected. There is also often a hydrostatic basic pressure which affects the introduced part of the pressure measuring device as a whole. The clinically relevant and prevailing pressure amplitudes, depending on the location of the application, for example in the coronary cardiovascular system, are in the amount of the difference between the systole and diastole, up to approximately 150 mmHg (corresponding to approximately 20 kPa), and in the vertebral canal, in the region of fine propagated vibrations through the cardiovascular system, are up to approximately 10 mmHg (corresponding to approximately 1333 Pa). Thus, in the available light frequency ranges of each optical waveguide material, for example in spinal surgical applications, more FBG sensors and, with narrower differences in the grating spacings thereof (i.e. in the Bragg wavelengths resulting therefrom in each case) can be used for example in coronary applications.

In addition, it can be advantageous for the measuring cell holder to comprise at least one marker made of a metal or transition metal, in particular a metal marker which is opaque to X-rays, and which is present in one or another layer of the measuring cell holder in order to make the position of the measuring cell holder in the biological system visible by means of an imaging method. By means of such introductions, the location of the pressure measuring device in the biological system can be determined, which can be advantageous for example when an operation on the biological system is carried out or planned, and data which are relevant to the operation are to be detected by means of the pressure measuring device. Thus in addition to the data about the pressures, the location and position of the pressure measuring device can also be detected in an imaging method and are displayed two or three-dimensionally for the clinician, preferably in a colour-coded manner, and in particular over the course of time. Especially when the measurements are carried out on biological systems in various positions, this correlation can be of considerable clinical significance.

Likewise, markers that are more opaque to X-rays, which are introduced in the path of the pressure measuring device, can facilitate retrieval under X-ray inspection if the pressure measuring device is accidentally torn off.

In the case of clinical issues, it is often important to learn whether a narrow point in the biological system has a clinical relevance. Measuring pressure amplitudes before and after a problematic narrow point in this case provides valuable information. In the region of the spine, it was possible to show that narrow points, which lead to a substantial ebb in the vibration amplitudes occurring in the spinal canal above the hydrostatic basic pressure, make surgery more necessary. In the region of the coronary intervention, narrow points which change the systolic compression wave propagation are often of clinical significance.

Due to the greater compatibility thereof with MRI examinations, transition metals such as tantalum can be advantageous as markers which are opaque to X-rays. Alternatively, MRI resonators can be integrated in the pressure measuring device so that the pressure measuring device is visible in an MRI examination. The markers can be attached to a layer in the pressure measuring device in the form of splints, sleeves or meshes. The markers, which are opaque to X-rays, can also be retrospectively connected to the pressure measuring device in a simple manner. However, the markers can also be introduced in the pressure measuring device in that the markers are added to the layers of the pressure measuring device for example as particles during production. The markers, which are opaque to X-rays, can also be attached to the pressure measuring device in such a way that they are in the form of markings, such as lines or rings, and can be used for optically reading the insertion depth of the pressure measuring device in the biological system.

In this respect, it can be advantageous for the metal marker to be used as a coating for the reference measuring cell at the same time, so that the reference measuring cell merely detects the effect of temperature on the fibre Bragg grating and, in addition, the coating can be used as a marker for an imaging method.

In one embodiment, the measuring cells can be produced from cost-effective telecommunications optical waveguides, for example having a commercially standard coating diameter of 80 or 125 am.

In one embodiment of the invention, the measuring cell holder can comprise a piezoelectric sensor in the first and/or second layer. The measuring cell holder can comprise a cable, for example a cable having copper conductors, in the layers thereof, in which one or more piezoelectric sensors are integrated. The piezoelectric sensors advantageously consist of piezoelectric ceramics (in particular modified lead zirconate titanate (PZT) or barium titanate) or of monocrystalline materials. Preferred monocrystalline materials are quartz, tourmaline, gallium phosphate and aluminium nitride. The preferred piezoelectric sensors have a high sensitivity and long-term stability. The piezoelectric sensors are preferably connected in series and are arranged inside the measuring cell holder, in particular inside the cable in parallel with a cable axis. Advantageously, the piezoelectric sensor, which is arranged at the end of the measuring cell holder which is remote from the evaluation unit, is attached transversely to the axis so that a pressure on the tip of the measuring cell holder can be detected by the piezoelectric sensor. As a result of the fact that the piezoelectric sensors are preferably connected to an electrical conductor, the diameter of the measuring cell holder also increases with the increasing number of sensors. In order to minimise the overall diameter of the catheter, the piezoelectric sensors can preferably be controlled one after the other by a bus system. In this case, digital circuits or simple logic modules can be used in order to activate each piezoelectric sensor.

In a preferred embodiment of the invention, the measuring cell holder comprises at least two layers, wherein the measuring cells are arranged in a first and/or a second layer. The measuring cell holder, in particular the optical waveguide or the cable comprises a plurality of layers. The optical waveguide consists of a core material, a cladding material and preferably a protective layer. The cable is preferably constructed from an electrically conductive region, a cladding region and preferably a biocompatible protective region which is attached to the cladding region. The biocompatible protective layer can be designed similarly to in the case of an optical waveguide. It has surprisingly become apparent that the measuring cells can be arranged in a first and/or a second layer of the measuring cell holder and, as a result, the sensitivity of the pressure measuring device and the local resolution capacity of the acting forces can be improved.

It could be shown that bends or temperature fluctuations in the measuring cell holder can bring about disruptions in the pressure measurement by measuring cells, in particular FBG sensors. It may thus be advantageous to detect the bends. A bend in the measuring cell holder simultaneously brings about an extension and compression of the measuring cell holder. Measuring cells which are introduced in or around the cladding, in particular FBG sensors, in the case of a bend can respond, regardless of the location thereof, with different reflected Bragg wavelengths, i.e. the FBG sensors which are located on the inside of the bend are in particular compressed, and the sensors which are located on the outside are stretched, which leads to two different reflection maxima. From the knowledge of this phenomenon, it is surprisingly possible to deduce the presence of bends in the measuring cell holder, in particular in the optical waveguide. Thus for example pressure measurement values in bent portions can be discarded. However, it can equally be advantageous to also detect the pressures in the bends. For example, by means of evaluation software, the user can be notified of the risk of disruption by a bend, and optionally the software can also analytically correct the pressure measurement values of the FBG sensors in the core region by determining the bend from the cladding. Furthermore, it can be advantageous for longitudinal movements and bends in the pressure measuring device to be able to be measured simultaneously by means of extension measurement technology so that it is possible to determine the location and shape of the introduced pressure measurement device. In a special embodiment, FBG sensors for measuring bends which are introduced into the optical-waveguide cladding in a circular manner and FBG sensors which are present in the optical-waveguide core at the same time can be used for measuring pressure. Furthermore, in one embodiment, for the sake of light frequency economy, split phenomena of the FBG sensors can be used for bend detection. In addition, the direction of the extension can be determined in that preferably fields of various FBG sensors are introduced in the cladding in a circular manner. In summary, surprisingly, the position on the pressure measuring device and the size and the direction of each bend can thus be calculated. In one embodiment of the invention, a measuring cell can be arranged at the tip of the pressure measuring device, i.e. at the end which is remote from the evaluation unit. Said measuring cell, for example an FBG sensor or a piezoelectric sensor or even a Fabry-Pérot interferometer, can be used to detect the pressure measuring device becoming stuck for example in the tissue early on, and to warn the clinician optionally by means of evaluation software. In addition, temperature artefacts can also be eliminated.

It can be advantageous for the measuring cell holder to comprise at least one working channel having an input and optionally an output. The measuring cell holder can comprise one or more working channels extending in particular in parallel with the longitudinal axis of the measuring cell holder. Via the working channel, material, for example medicines, can be introduced into the biological system or also removed therefrom. Furthermore, miniature devices or optical or light-energy-conducting systems, and guide wires can be introduced or dilations can be carried out by means of one or more balloons which are attached to the outer wall of the measuring cell holder or are introduced into the outer wall of the measuring cell holder. It would also be possible to introduce and place stents. Equally, by means of electrodes which are also only temporarily introduced, discharges, stimulations or coagulations can be carried in the biological system. The electrodes and the cables thereof can also be produced from conductive transition metals. The application of medicines can advantageously also be carried out by means of the pressure measuring device, in particular by a working channel. It is also possible to carry out targeted endoluminal sclerotherapy of varicose veins by means of the pressure measuring device, in particular by means of one or more working channels. The working channels can comprise the respective outputs thereof laterally at the tip of the pressure measuring device or in the path of the pressure measuring device. In order to prevent disruptions, for example in MRI scans, electrodes can be introduced into the pressure measuring device only shortly before use and then optionally removed again.

Equally, in one embodiment, one or more electrodes can be permanently attached to the pressure measuring device. In a further embodiment, the working channel comprises a plurality of output openings, for example in order to evenly distribute liquids introduced via said openings in the organism or, when abutting tissue structures, in order to have alternative discharge options available.

In a preferred embodiment of the invention, the measuring cell holder is connected at the end which is close to the evaluation unit by a coupler, a connector or circulator to a light source and an optical sensor. The control of the FBG sensors is preferably carried out by means of conventional light sources, such as respectively fibre-coupled, adjustable narrow-band lasers or broad-band light sources, such as superluminescent light-emitting diodes (SLEDs). In one embodiment, the pressure measuring device can additionally have a sterilisable optical plug connection, for example a modified FC/APC (angled physical contact) connector. The adjustable narrow-band light source requires the light source to be matched to the expected reflection wavelength of each FBG sensor and a, preferably continuous, adjustment in a narrow range over and/or above said wavelength, in order to measure a change in the reflection maximum of each FBG sensor (for example as scanning). This means it is advantageously possible to activate individual FBG sensors in each case using the corresponding narrow wavelength range. Equally, it is advantageously possible to control a plurality of different FBG sensors at the same time using light from a broader wavelength range.

The evaluation of the wavelengths reflected by the FBG sensors can preferably be carried out by means of known optical sensors, wherein, depending on the light source used, a photosensor or a system consisting of a light-frequency separator and a sensor (for example a monochromator and charge-coupled device (CCD) line(s)) can be used. The light source and the sensor are connected in particular by a coupler or a circulator and a connector to the optical waveguide. The detection of the data and the evaluation can be carried out by means of a data processing unit, wherein on the basis of the reflection light wavelengths and/or peak measurements and by means of an allocation of the measurement values to the corresponding measuring cells, the resulting pressure ratios are calculated on the basis of the changes in the measurement values, in particular with reference to a standardisation variable. The data processing unit advantageously obtains measurement results continuously or intermittently, for example at 50 Hz per measuring cell, about the grating state of each of the FBG sensors in the measuring cell. As a result, it is possible to draw conclusions regarding the pressure ratios relative to the location of the measuring cell holder in the biological system, and in addition to make assertions relating to the temperature. Advantageously, a pressure measuring system is also provided, comprising a measuring cell holder having measuring cells, a light source, an optical sensor, an optical coupler or circulator and a data processing unit, optionally a memory, and optionally power and communication supplies. Furthermore, by means of a corresponding hardware and/or software interface, a correlation can be produced between a measured heart rate and the pressures measured by the pressure measuring device, the pressure measuring device being triggered by ECG or pulse waves. Equally, other dynamics of the organism can also advantageously be used to trigger the device, for example breathing or movements. The measurements detected by the pressure measuring device can be transmitted periodically or continuously to a device which is arranged outside the biological system, wherein, depending on the configuration of the pressure measuring device, pressures, temperatures, spatial changes, oscillations, vibrations and/or damage to/tearing of/destruction of the pressure measuring device can be measured.

As the scanning frequency of the measuring cells increases, the pressure curves can be shown increasingly well in particular over time with the progressions of the amplitudes thereof. Optionally, by means of interpolation, amplitudes can be shown in such a way that they are easier for the examiner to read, and thus lower scanning frequencies are compensated to a certain extent. The assessment of the progressions of the amplitudes can allow the examiner to draw further conclusions regarding the functionality of the examined biological system.

In a preferred embodiment of the invention, a measuring cell, in particular an FBG sensor or a piezoelectric sensor, is integrated in the tip of the first end of the measuring cell holder, wherein the sensor is transverse to the longitudinal axis of the measuring cell holder or in an axial direction relative to the longitudinal axis. The sensor can be used in particular to establish contact between the pressure measuring device and for example a boundary or boundary face of a biological system, which in turn can be required for guiding the pressure measuring device in the biological system.

Furthermore, it is preferable, depending on the field of application of the pressure measuring device, to arrange the measuring cells, in particular the FBG sensors, in the measuring cell holder with various grating spacings, said measuring cells being adapted to the different pressure ratios which are present in a biological system. In addition to varying grating spacings, the adaptations can also include spacings between a plurality of FBG sensors.

Advantageously, at least two measuring cell holders can be arranged in the protective layer consisting of a biocompatible material, wherein it is also preferable for at least three measuring cell holders to be arranged in the protective layer consisting of a biocompatible material. The protective layer can be for example a plastics envelope, wherein other materials such as metal can also be used. The pressure measuring device can thus be configured in such a way that a plurality of measuring cell holders are surrounded by one protective layer or envelope. The measuring cell holders, in particular the optical waveguides, can be extruded together. For this purpose, the, i.e. a plurality of, optical waveguides are located in a sleeve, wherein however it is also possible to carry out production in the injection moulding of the active sensory part of the optical waveguide, i.e. in particular of the region in which a measuring cell is arranged. By means of this production method, it is also easy to add or introduce a working channel. Furthermore, it can be advantageous to construct the pressure measuring device coaxially, so that a plurality of measuring cell holders are arranged around a working channel, and the working channel can be filled with stiffening means, for example with rigid catheters, in a variable manner and according to the application in each case, and thus the stiffness of the pressure measuring device can be adapted. The FBG sensors can be oriented in a parallel, helical or spiral manner, singly, multiply or three-fold, relative to or about a working channel of this type.

A further advantageous embodiment consists of at least three measuring cell holders which are arranged coaxially around an inner, central structure with approximately equal spacings, for example at 0°, 120° and 240°. This structure can be an additional measuring cell holder and/or a working channel. The coaxially arranged optical waveguides can preferably be used in this case to measure the shape/bend of the pressure device, but also to measure pressure, whereas the inner, central cable can be in the form of a measuring cell holder and can be used to measure pressure or/and as a temperature reference. Equally, in a further embodiment, the inner measuring cell holder can be in particular in the form of an optical waveguide or also an electric conductor, and can also or only be used to supply a tip sensor or a Fabry-Pérot interferometer.

In this respect, it is preferable for the measuring cell holders to be arranged so as to be offset from one another in the longitudinal direction of the protective layer. The protective layer has a longitudinal direction and, within the meaning of the invention, can also be referred to as a protective envelope. The measuring cell holders, i.e. in particular the optical waveguides, are arranged eccentrically relative to one another in the protective envelope. In particular, the FBG sensors which are present in an optical waveguide are arranged so as to be offset from FBG sensors of a second and optionally at least one additional optical waveguide. It has been found to be particularly advantageous for the measuring cell holders to be arranged so as to be offset from one another by 1/n of a pitch of an FBG sensor, where n is the number of measuring cell holders in the protective layer. A pitch is in particular the distance from the centre of an FBG sensor field to the centre of the next FBG sensor field within the same measuring cell holder, an FBG sensor field being a uniform grating having the same grating width. This surprisingly makes it possible to detect and separate changes in the reflection wavelength of an FBG sensor as a result of bends, extensions and radial forces, and results both in an improvement in the spatial resolution and also in sensors of the FBG sensors which are locally interruption-free through the parts of the pressure measuring device which are equipped with FBG sensors, as it provides an arrangement of the FBG sensors at the same height in each case over various measuring cell holders. Pressures can thus be detected in a substantially interruption-free manner along the measuring cell holder.

In order to achieve easy guiding of the pressure measuring device in for example a biological system, the pressure measuring device can comprise a stiffening means, for example in the working channel or the protective envelope. In this case, said means can be a wire-shaped means made of plastics material, which is arranged for example centrally in the pressure measuring device, in particular in the protective envelope. As a plastics material for the stiffening means, for example polymers or aromatic polyamides can be used. The stiffening means can also be designed to be web-shaped. A web made of the previously mentioned preferred plastics materials lends itself in particular to this case. The stiffening means is advantageous in particular when a plurality of measuring cell holders are present in the pressure measuring device, in particular in the protective envelope.

In order to determine deformations or forces acting on the pressure measuring device at the tip of the pressure measuring device, it may be preferable for an interferometer to be arranged in the end which is remote from the evaluation unit, wherein when an atraumatic tip is present, the interferometer can also be arranged in the atraumatic tip. The interferometer can be in particular a Fabry-Pérot interferometer or a Michelson interferometer, wherein any other multiple-beam interferometers can also be used. The Fabry-Pérot interferometer comprises at least one optical resonator which is formed from two semi-permeable mirrors. In the tip or the fibre end of the pressure measuring device, a reflector, i.e. a light-reflecting surface, is additionally arranged. It may also be preferable to design the reflector as part of the Fabry-Pérot interferometer. The Fabry-Pérot interferometer can be produced as a microsystem (micro-electro-mechanical system—"MEMS"), i.e. as a miniaturised device, the components of which have the smallest possible dimensions (in the micrometer range) and work together as a system. It is also possible to produce the interferometer by depositing thin layers with an air gap at the tip by means of thin-layer technology. The Fabry-Pérot interferometer thus forms, in addition to the measuring cells arranged in the measuring cell holder, a further measuring cell which is arranged substantially at the tip (the end which is remote from the evaluation unit) or the fibre end. In one embodiment, the Fabry-Pérot interferometer forms a pressure sensor which can be evaluated in the same wavelength window as the FBG sensors. In the tip or the fibre end, there is a Fabry-Pérot interferometer, which was produced for example in microsystem technology, which interferometer is composed of at least one end of a measuring cell holder, in particular of an optical waveguide (end which is remote from the evaluation unit) and at least one mirrored membrane which can be deformed by the effect of pressure and consequent deformation of the tip. At the optical waveguide end, i.e. the end of the pressure measuring device which is remote from the evaluation unit, partially reflective mirrors can be arranged, the transmission spectrum of which preferably exhibits narrow transmission maxima for wavelengths, which meet resonance conditions, whilst other spectral ranges in the transmission are almost completely eliminated. This takes place by means of constructive or destructive interference of the partial beams. As a result of the fact that the mirrored membrane is designed to be deformable, an acting force (for example a pressure) brings about a change in the transmission spectrum and consequently of the reflected beams, so that even low changes in pressure at the tip or the fibre end can be measured. This is advantageous in particular when introducing the pressure measuring device into a biological system and when guiding the pressure measuring device through said system. In addition, the interferometer is substantially resistant to temperature influences, which means, by means of the interferometer, a pressure can be measured independently of the temperature. The interferometer can thus be used to calibrate the pressure measuring device to temperature artefacts and to measure other pressure ranges and other pressure resolutions, optionally also in other measuring frequencies.

The interferometer can be used to calibrate the pressure measuring device, since the interferometer is influenced by temperature to a much lesser extent than the FBG sensors. In addition, other pressure ranges, for example narrower or broader pressure ranges, can be measured by the interferometer at the tip of the pressure measuring device. This can be used for detecting contact with tissue and for measuring absolute pressure values within the biological system.

In addition to measuring pressure, the FBG sensors can also be used in the pressure measuring device to establish location and shape, since conclusions can also be drawn about the location and shape of the pressure measuring device by means of the measured FBG data.

In a further aspect, the invention relates to a method for measuring a pressure in a biological system, wherein a radially flexible measuring cell holder is introduced into the biological system and is positioned at a first measuring point, wherein a first measurement result is captured at the first measuring point. A second measurement result is captured at a second measuring point at a measuring distance. The measuring cell holder is introduced into a biological system and positioned at a measuring point. At the first measuring point, a first measurement result can be captured. As a result of the fact that a measuring distance can be measured by means of the method, two measurement results can be determined in spatial or temporal dependence. As a result of a change in location of the measuring cell holder, advantageously the second measurement result can be captured at a measuring point which is at a distance from the first measuring point. As a result, it is surprisingly possible to capture two measurement results, in particular pressures, in relation to one another. One of the two measured pressures can be used for example as a local reference value in each biological system or in each portion of the biological system.

Furthermore, it is advantageously possible, without changing location, to capture a temporal measurement result at the first measuring point, wherein a second measurement result is captured at the first measuring point at a later time than the first measurement result. As a result, pressures can be measured at a measuring point over a course of time. By means of a preferably automatic shift of the measuring cell holder lengthwise or in particular of the measuring cells within an additional cladding by the length of the distance between two measuring cells, ambient pressure values can be captured in a spatially continuous manner.

By means of the preferred method, measurement results can advantageously be captured over a course of time, wherein, in addition, a change in location of the measuring cell holder or the biological system (in particular of a patient) can take place (for example sitting/lying down/standing, prone/supine position, or specific movements and loads).

Furthermore, by coupling the measuring data with imaging data from imaging methods (firstly detection of the location of the measuring cell holder, secondly detection of the morphology of the biological system), the ambient pressure data, in particular also the differences in pressure amplitudes, are shown graphically, for example are shown in colour. In conjunction with the grey-scale value information from the imaging, it can surprisingly be made possible in this case for the clinician to easily read the information. By introducing materials which are more opaque to X-rays at specific points of the pressure measuring device, a positioning and a determination of location and extension can also take place. By means of a software, in particular by means of a method for image generation, the position and/or shape of the pressure measuring device can be combined with additional measuring data to form a two-dimensional or three-dimensional image; optionally also over the course of time. For the image generation, the data of the pressure measuring device, in particular of the pressure measuring system in combination with additional data, for example from imaging methods, can be evaluated by means of a data processing unit and displayed graphically on an output unit, for example a monitor. Furthermore, image colour-coding of the differences in amplitude and pressure ratios captured by the pressure device is preferable. The data of the pressure measuring device can also optionally be presented acoustically.

The pressure measuring device according to the invention and the method can be used in different biological systems, wherein no substantial modifications have to be made to the pressure measuring device. Furthermore, the pressure measuring device can be sterilised, since the measuring cells and the measuring cell holder withstand the high temperatures of conventional sterilisers and the conditions of chemical and/or physical sterilisation unharmed and retain full operability. This is to be considered particularly advantageous with respect to the known pressure measuring devices, since they are often designed to be disposable and as a result lead to high costs. By contrast, the pressure measuring device according to the invention can be sterilised easily and quickly by means of known sterilisation methods.

However, it can also be advantageous for individual applications or biological systems if the pressure measuring device is designed to be disposable. In order to achieve safe and effective sterilisation of the pressure measuring device, the pressure measuring device can be connected to a support device in the steriliser. After successful sterilisation, the pressure measuring device can be stored, for example in a rolled-up state, in a storage or transport means until the next pressure measurement. Such a means can be for example a small tube, which the pressure measuring device can be slid out of and slid back into.

Advantageously, the method, or the pressure measuring device for evaluating the differences in the biologically occurring (in particular pulse-dependent) pressure amplitudes can be used at the various measuring points of the pressure measuring device. The intermediate result measured in this manner can in turn allow conclusions relating to location(s) and clinical significance, for example of lumbar spinal stenoses or coronary vessel stenoses.

It has surprisingly been found by means of experiments that the following uses inter alia of the pressure measuring device and the method are possible: cardiology/cardiac surgery (for example pressure measurement in coronary vessels, intra-auricular pressure measurement, intravascular ultrasound), blood pressure measurement with horizontal sensors (absolute and in the course of the vessel, resolved in time and space); phlebology/angiology (for example invasive intravenous/intra-arterial pressure measurement and application of medicines, endosonography, bougienage and balloon dilatation)/vascular surgery (for example intraoperative pressure measurement in carotid surgery, endosonography); gastroenterology (for example pressure measurement in the upper gastrointestinal tract, for example in the case of dysphagia or secondary disorders in the movement path of the oesophagus, diagnosis in the case of reflux oesophagitis, investigating pains in the chest area, for example also of a non-cardiac nature, endosonography, bougienage and balloon dilatation): abdominal surgery (for example in the case of reflux oesophagitis, before and after surgery in each case, and in the case of abdominal compartment syndrome after aorta surgery); proctology (for example pressure measurement in the lower gastrointestinal tract, abdominal pressure measurement in the rectum, endosonography, bougienage and balloon dilatation); endocrinology/diabetology (for example diabetes diagnosis, endosonography, bougienage and balloon dilatation); pneumology (for example pressure measurement in the case of pulmonary emphysema): thoracic surgery (for example pressure measurement in the pulmonary circulation, for example in the case of pulmonary artery stenosis, endosonography, bougienage and balloon dilatation); nephrology (for example intratubular, intravesical and intraurethral pressure measurement, endosonography, bougienage and balloon dilatation, dialysis indication); urology (for example urinary incontinence, postoperative stress/urge incontinence, detrusor instability, neurogenic bladder dysfunction, subvesical obstruction, diurnal and nocturnal enuresis); gynaecology/obstetrics (for example endosonography, bougienage and balloon dilatation, for example for fertility diagnosis/treatment, intrauterine pressure measurement, for example for diagnosing labour activity and/or simultaneous continuous amnioinfusion); neurology/psychiatry/neurosurgery (for example intracranial diagnosis and treatment); pain medicine/spinal column surgery (for example diagnosis/treatment of spinal stenosis/changes in intervertebral discs); rheumatology (for example endosonography, bougienage and balloon dilatation, for example in the case of rheumatic disorders of the upper/lower gastrointestinal tract); orthopaedics (for example intra-articular pressure measurement in the hip joint, functional compartment syndrome of the muscle compartments, intraosseous pressure measurement); traumatology (for example traumatic compartment syndrome of the muscle compartments); paediatrics/paediatric surgery (for example investigating urinary bladder function disorders, for example in the case of Hirschsprung's disease, primary disorders in the movement path of the oesophagus for example in the case of achalasia, diffuse oesophageal spasm or nutcracker oesophagus, endosonography, bougienage and balloon dilatation); otorhinolaryngology (for example tinnitus diagnosis, diagnosis in the case of Eustachian tube disorders, endosonography); oral and maxillofacial surgery (for example intracranial pressure measurement in the case of optic nerve lesions); ophthalmology (for example intraocular pressure measurement); haematology/oncology (for example endosonography, for example before fine needle biopsy); anaesthesia (for example neuromonitoring, invasive intravenous/intra-arterial pressure measurement and application of medicines, intrapulmonary/intratracheal/intrapleural pressure measurement); radiology (for example diagnosis of portal hypertension, interventional radiology); continuous cerebral pressure measurement in a Spitz-Holter valve); continuous/intermittent blood pressure measurement, measurement in various vessel portions (including intracerebral); continuous/intermittent incontinence diagnosis (urological/proctological); intestinal function diagnosis (strength, frequency, duration of peristalsis), presence of an irritable colon; gynaecological monitoring of for example the uterus, ovaries, fertility, children; measuring stress and vibrations and deformation at implants (plates and nails on fractured/osteotomised bones) and endoprostheses; function diagnosis, assessing the consolidation, feedback for controlling loads and movements, temperature, wear and friction control; installation of the pressure measuring device in orthoses/bandages/inserts/braces for measuring stress and movement, and documentation; control of exoprostheses in the shaft or in the artificial joint in order to stabilise an intelligent sensor control; coupling endoprostheses and exoprostheses, in the case of ill or paralysed patients by means of the pressure measuring device; installation of the pressure measuring device in protectors (sport/research) or special clothing; use of the pressure measuring device for an "artificial intelligence interface", so that body movements in the form of pressure, contact, vibrations, location and/or temperature are transmitted and can be used for robots/machines. It is also possible to use the pressure measuring device as an implant. In this case, part of the pressure measuring device or the complete pressure measuring device in combination with a data collection system, power supply and optionally transceiving means can be integrated in a biological system as an implant so that for example it is possible to carry out monitoring of structures of prostheses over a course of time. By means of an implanted pressure measuring device of this type, it is also possible to carry out a continuous measurement for example of blood pressure and pressure in the ventricles, by means of which it is possible to achieve long-term blood pressure measurement.

By means of the continuous evaluation of the pressure curves, which are recorded in the context of time and space, of a natural pressure wave or a pressure wave which is generated at the catheter by a suitable device, a conclusion relating to the surrounding tissue can also be drawn. For this purpose, the characteristic parameters of the pressure curve and/or the spatial reflections of the pressure wave or pressure waves can be registered and evaluated so that the properties of the walls as a whole (for example calcification, stenoses, scarring) and in the depth extension (quantity and quality of intimas and plaque, thickness of the vessel interior wall media) can be determined therefrom similarly to in an ultrasound measurement. In a further embodiment, for example by means of the pressure measuring device supplemented by piezoelectric sensors, one or more pressure pulses can be transmitted into the organism, and the measurement results of the measuring cells of the pulses reflected in the organism can be evaluated.

In the following, a preferred use of the pressure measuring device is to be illustrated with reference to an example. A difference in pressure at a problematic narrow point in a coronary vessel of a person is to be measured. In order to introduce the pressure measuring device into the bloodstream, a puncture site can advantageously be anaesthetised locally. The extent to which an anaesthetic should be used depends in each case on the type and the location of the pressure measurement. It may be preferable to introduce the pressure measuring device into the human organism via a sheath so that it is possible to change the pressure measuring device if said device is damaged or if other devices are to be used in addition. The sheath is used in particular as a flexible guiding rail, through the inside of which the pressure measuring device can slide, wherein the puncture site is sealed at the same time. The pressure measuring device is now introduced. The tip consists of soft, rounded material (for example a plastics material) so that the risk of damage to the inside of the blood vessels is as low as possible.

Since the pressure measuring device is in particular an optical waveguide, in particular an optical or electrical conductor, for example a cable, and preferably comprises a metal marker, the pressure measuring device can easily be seen in these embodiments during X-ray radiation. A cardiologist can thus observe the position of the pressure measuring device in the person, the patient, very well when sliding the pressure measuring device through the blood vessel system towards the heart or towards the coronary vessels. Advantageously, although the measuring cell holder has radial flexibility, it is designed to have a constant length. This means that under the effect of a propulsive force, such as being slid into the blood vessel, the pressure measuring device is not compressed to a significant extent. Since the coronary vessels themselves are difficult to see, it may be necessary for the cardiologist to briefly make local vessels visible by adding a contrast agent. The contrast agent can advantageously be introduced via a working channel of the pressure measuring device. In addition, by means of an electrocardiographic coupling, found in the prior art, of the biological system with the fluoroscopy system, the heart and the vessels thereof can be shown in each case in the same functional position (systole/diastole).

It may be preferable for a guide wire to be introduced through a working channel of the pressure measuring device, which acts as a support when guiding the pressure measuring device through the vessels. For this purpose, the tip of the pressure measuring device can in particular be bent. The guide wire keeps the bent tip of the pressure measuring device preferably straight as long as the wire is located inside the working channel.

If the guide wire is pulled out bit by bit by the cardiologist, the tip of the pressure measuring device assumes the preferred, for example bent, shape thereof. By repeatedly pushing in and pulling back the wire and the pressure measuring device, the cardiologist can "bend" in a targeted manner and explore at the desired point, which is particularly advantageous when examining the coronary vessels—lastly in this case, the correct branch must be "reached" in order to be able to be able to move forward. Depending on the targeted point, differently bent shapes are used. If the cardiologist has arrived at the point where the stenosis is expected to be, pressure measurements can be carried out, the indication can be confirmed, and subsequently an intervention can optionally be carried out.

Depending on the forces acting on the measuring cell holder, the measuring cell behaviour of the measuring cells changes, which in turn can be converted into pressure measurement values in conjunction with a data processing system. As a result, the pressure in a vessel can be determined, and changes in pressure amplitudes can be detected, as caused for example by clinically relevant narrow points. The pressure measuring device can measure the pressure at a measuring point, wherein the pressure measuring device can then be moved on to another measuring point so that two pressures can be detected at two measuring points. The measured pressures can be juxtaposed in order for example to establish a difference in pressure caused by a malfunction.

The pressure measuring device can carry out pressure measurements in spatial dependence. However, it may also be preferable to carry out pressure measurements in temporal dependence, in particular when a plurality of pressures are detected at a measuring point one after the other over time. As a result, a time curve of the pressure at a measuring point can be determined. The measurement of the pressure by the pressure measuring device can thus also be carried out using only one measuring cell, wherein it is preferable for the pressure measuring device to comprise at least two measuring cells, and for one of the two measuring cells to be configured as a reference measuring cell for measuring the effect of temperature on the measuring cell. The actual pressure measurement is then carried out using only one measuring cell, in particular an FBG sensor. The pressure measuring device preferably comprising FBG sensors can take place over a measuring portion of several to many centimeters so that a stenosis (flow/pressure value) can be located in terms of direction and extension. By means of a working channel of the pressure measuring device, a balloon with or without a stent can preferably be positioned with the preferred aid of data from imaging methods (X-ray source assemblies, MRI or computer tomography (CT)) and extended using pressure control. The pressure data/pulse curves can advantageously be projected onto the pressure measuring device in the imaging system of the imaging methods. Furthermore, it is possible to carry out activation of the measuring points similarly to in a flow measurement in the echocardiogram.

After the examination, the pressure measuring device is removed from the vessel and the patient, and the puncture site is covered for example by a compression bandage.

Figure 2:
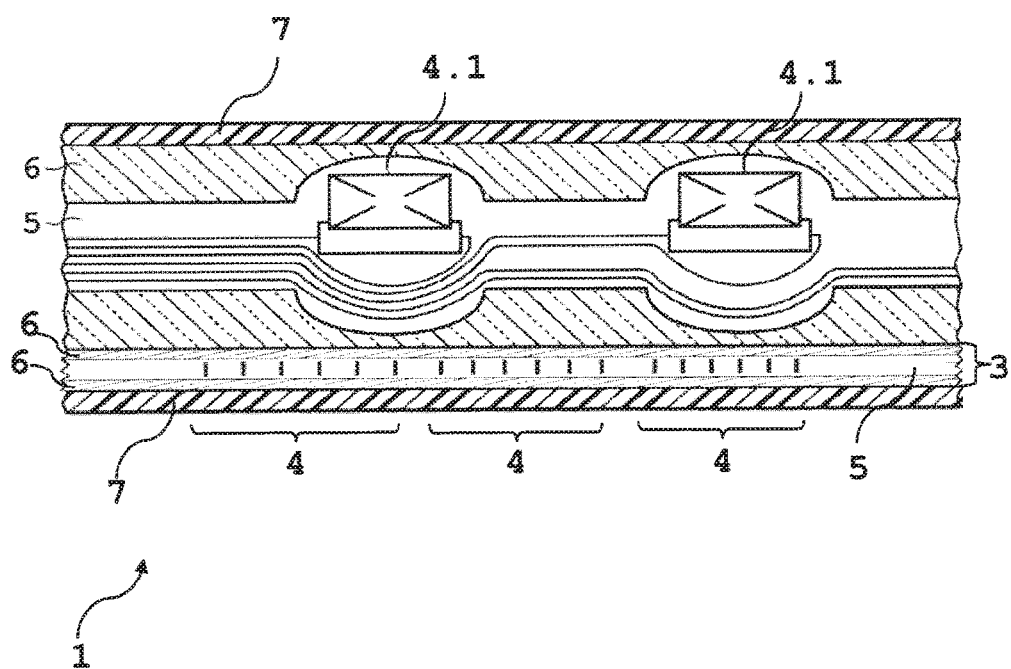
Figure 3:
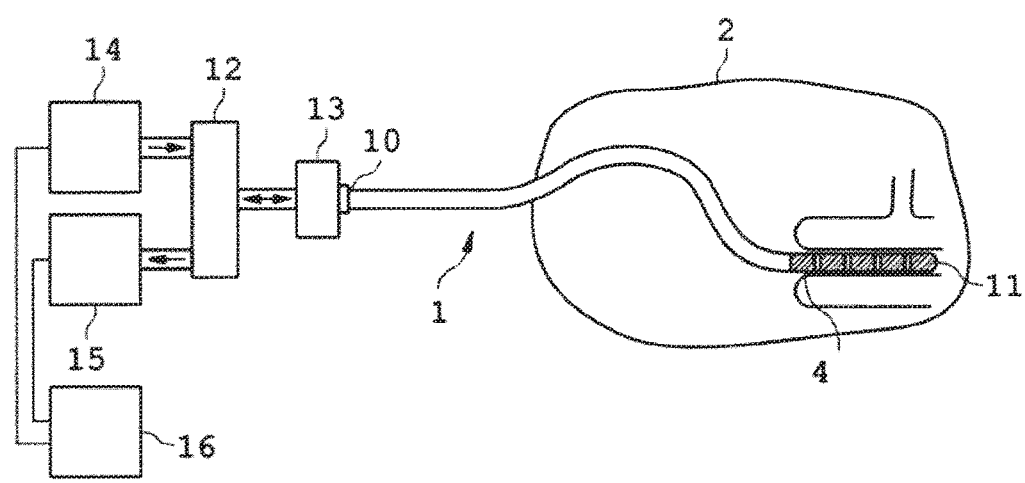
Figure 4:
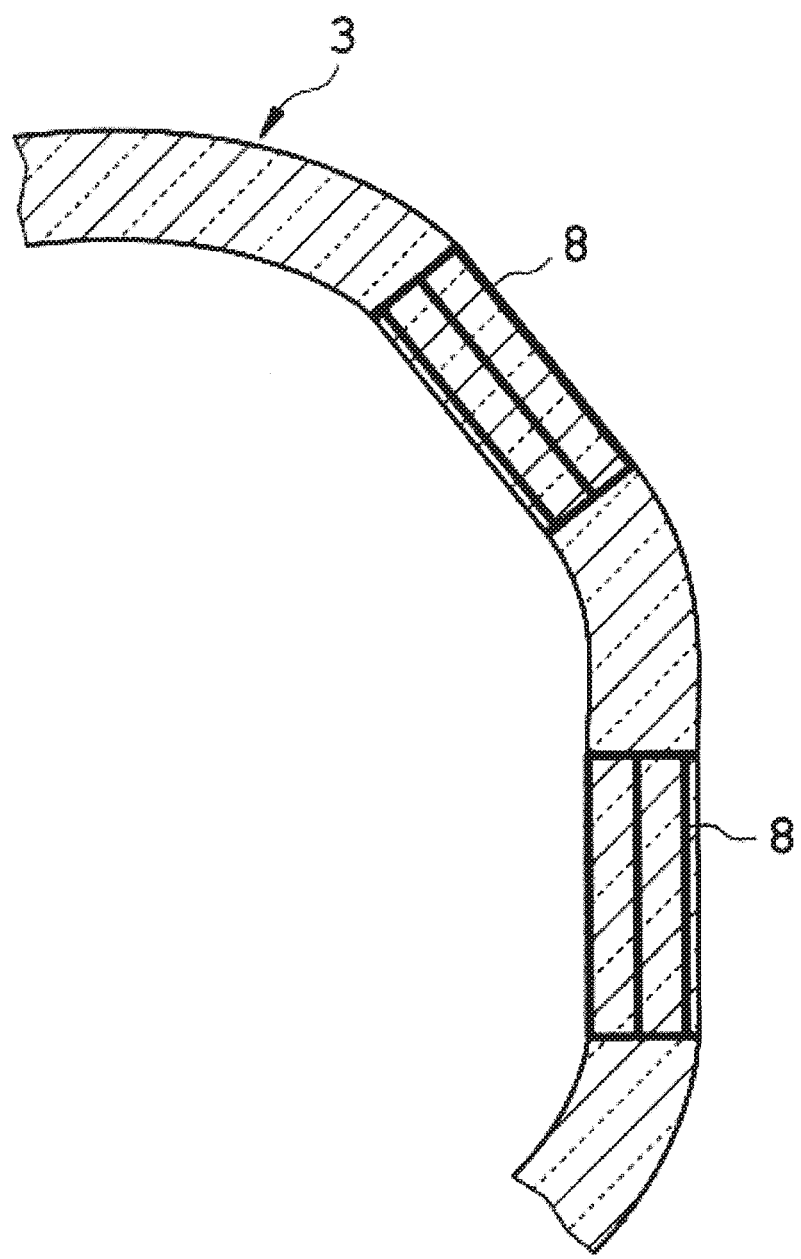
Figure 5:
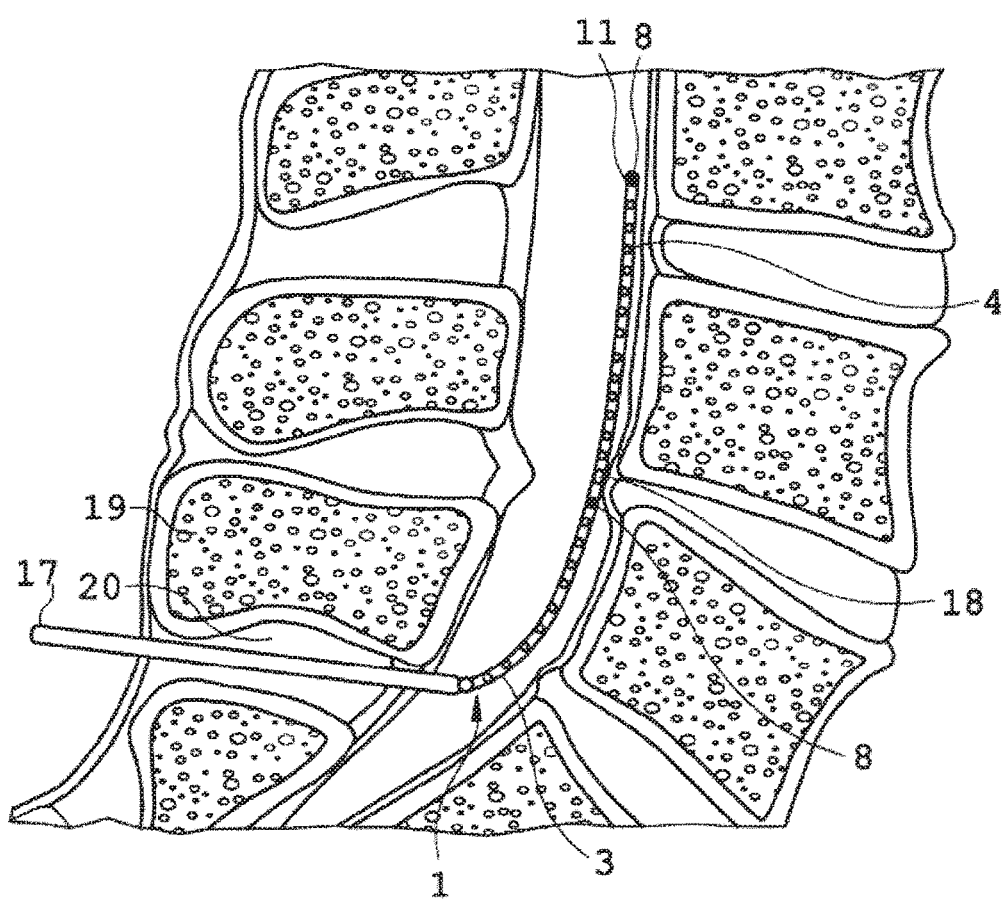
Figure 6:
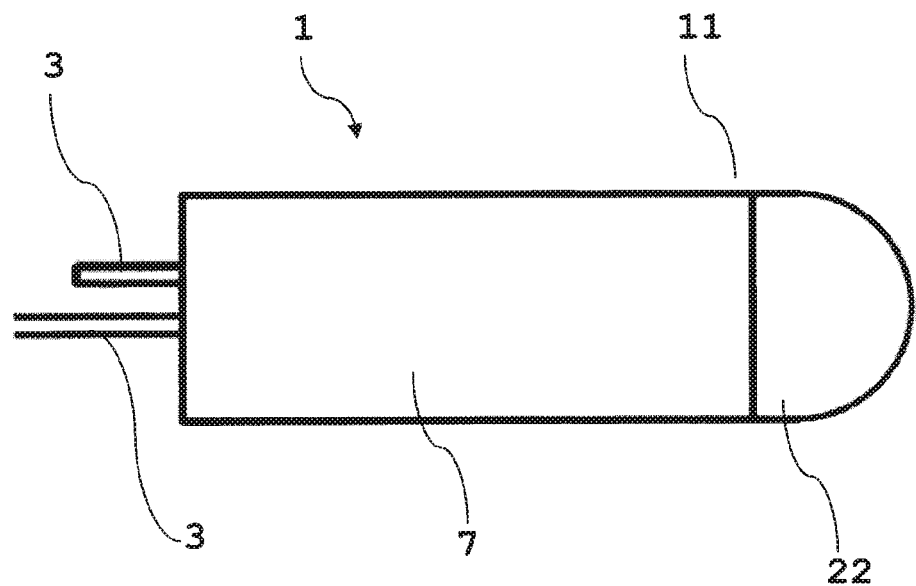
Figure 7:
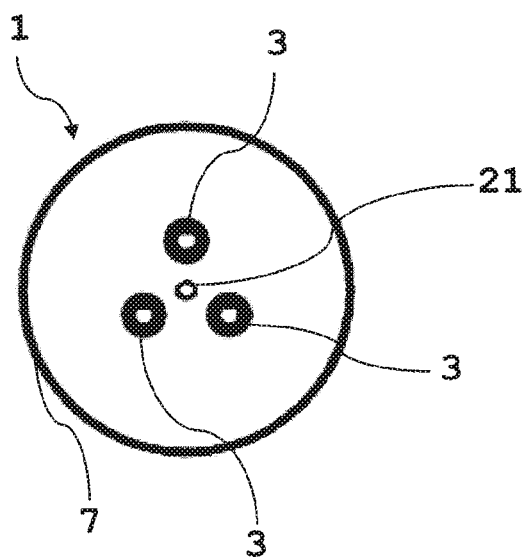
Figure 8:
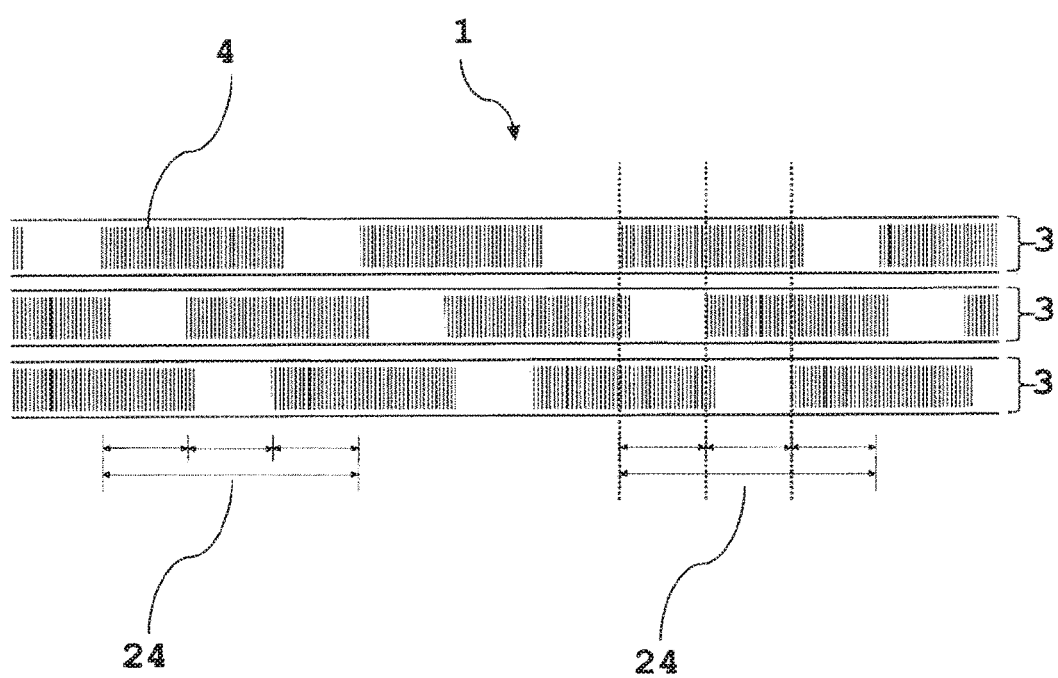
Figure 9:
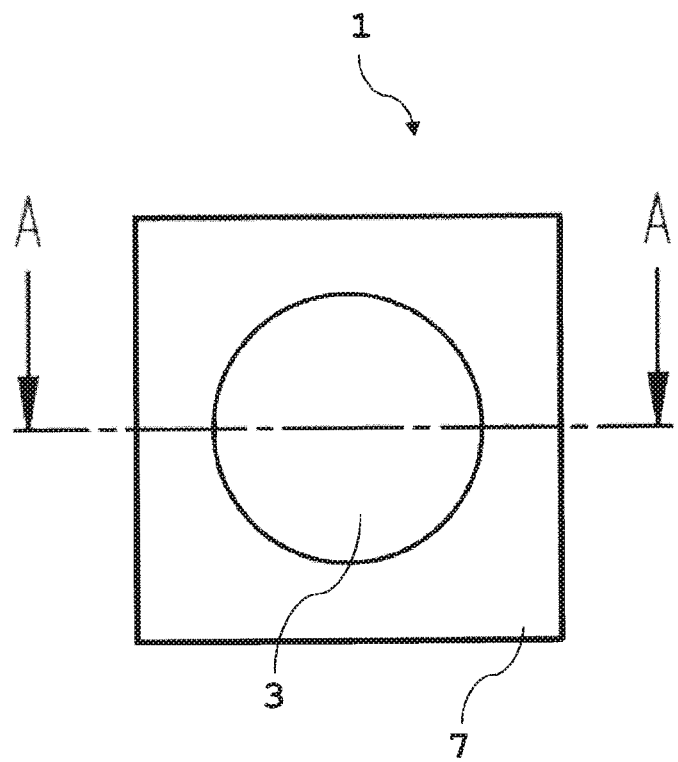
Figure 10:
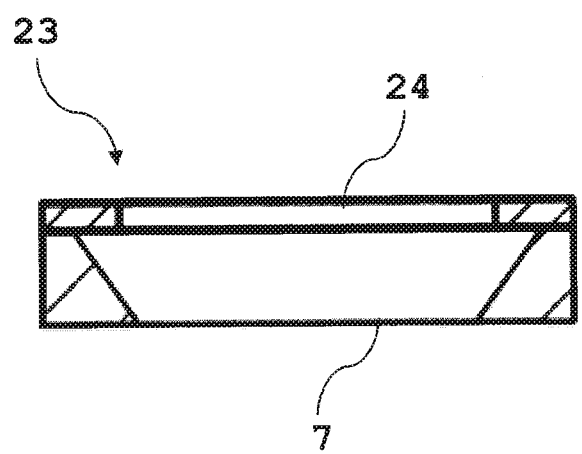
Figure 11:
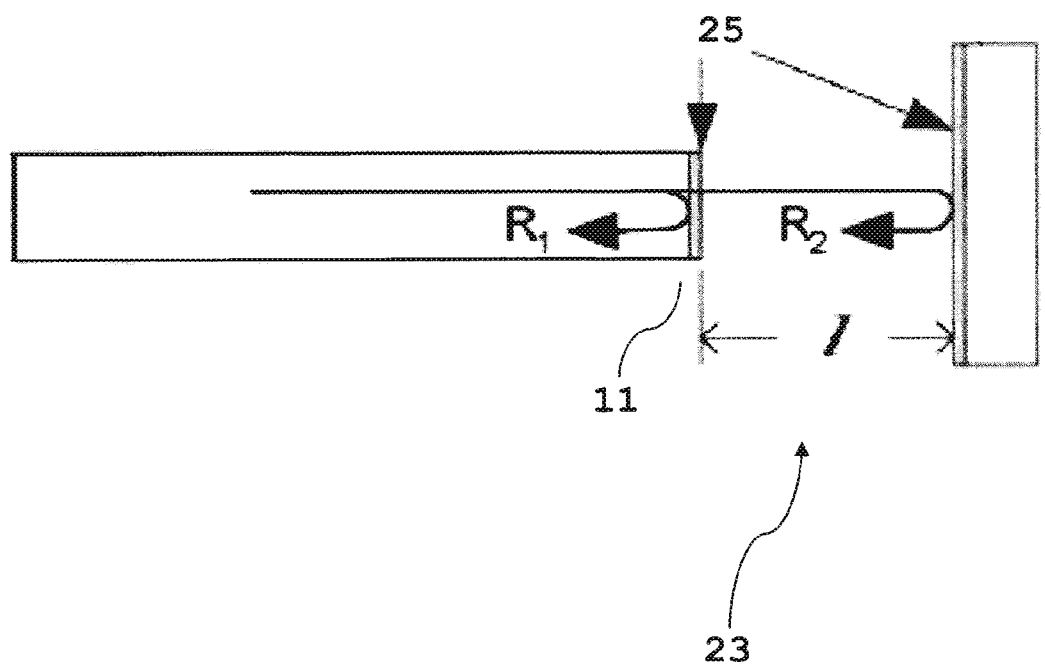
Figure 12:
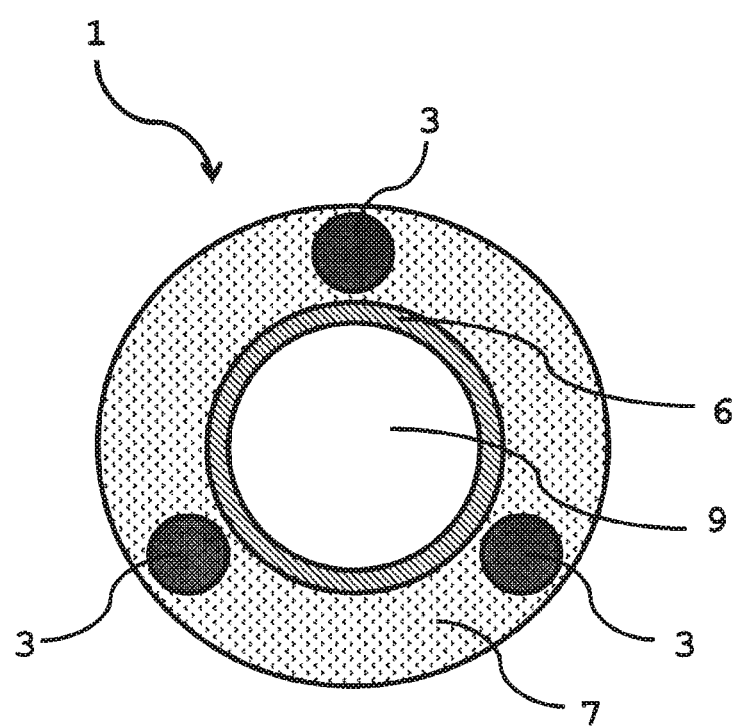

The invention will be described in greater detail below with reference to embodiments which are shown in the drawings. In the drawings:

FIG. 1 shows a pressure measuring device comprising FBG sensors,

FIG. 2 shows a pressure measuring device comprising FBG sensors and piezoelectric sensors, FIG. 3 shows a pressure measuring system in a biological system, FIG. 4 shows a pressure measuring device comprising a coating, FIG. 5 shows an example of an application for measuring epidural pressure, FIG. 6 shows a pressure measuring device comprising a protective envelope and an atraumatic tip, FIG. 7 is a sectional view of a pressure measuring device comprising a stiffening means, FIG. 8 shows an arrangement of a plurality of measuring cell holders in a protective envelope with an offset of 1/(number_of_measuring_cell_holders) of the pitch relative to one another, in the example of 3 measuring cell holders, thus an offset of ⅓ of the pitch, FIG. 9 to FIG. 11 are views of a Fabry-Pérot interferometer, and FIG. 12 is a sectional view of a pressure measuring device comprising three measuring cell holders.

FIG. 1 is a schematic view of a pressure measuring device comprising FBG sensors, and FIG. 2 is a schematic view of a pressure measuring device comprising FBG sensors and piezoelectric sensors. The pressure measuring device 1 comprising the measuring cell holder 3 is designed to be flexible or resilient, so that a force acting radially on the measuring cell holder 3 brings about an extension of the FBG sensors 4 which are arranged at a distance from one another in the measuring cell holder 3. In addition to the FBG sensors 4, piezoelectric sensors 4.1 can also be present in the pressure measuring device 1, wherein in FIG. 1, a pressure measuring device 1 comprising FBG sensors 4 and, in FIG. 2, comprising piezoelectric sensors 4.1, is shown.

The FBG sensors 4 are in the form of grating structures in a measuring cell holder 3 which is in the form of an optical waveguide.

The FBG sensors 4 are preferably configured in such a way that they have different grating structures and consequently different Bragg wavelengths and thus reflect different wavelengths. As a result, the FBG sensors 4 can either be activated individually using a corresponding wavelength or using broadband light sources. As soon as a force acts on the measuring cell holder 3, this leads to an extension of the measuring cell holder 3, i.e. of the FBG sensor 4 or of the piezoelectric sensor 4.1. In the case of the FBG sensor 4, this extension leads to the sensor reflecting a wavelength which is different from the original Bragg wavelength, which in turn is detected and converted into an acting pressure.

In the case of the piezoelectric sensor 4.1, which is arranged in an electrically conductive cable, as a result of the directed deformation, dipoles form within the elementary cells (shift of the charge focal points). The accumulation over the electric field connected thereto in all elementary cells of the piezoelectric sensor 4.1 leads to a measurable voltage. A large number of piezoelectric sensors 4.1 can be connected in series in a cable. As a result of an increasing number of piezoelectric sensors 4.1 combined with a number of supply and discharge lines, however, the diameter of the pressure measuring device 1 also increases. In order to minimise this, the piezoelectric sensors 4.1 can be activated one after the other by a bus system. By means of the measuring cells according to the invention, it is possible to carry out a simple and reliable pressure measurement in a biological system. The pressure measuring device 1 can comprise one or more working channels 9, via which for example a guide wire or a stiffening means can be introduced, or a medicine can be applied.

In order to increase the sensitivity of the pressure measurement, the FBG sensors 4, or in combination with the piezoelectric sensors 4.1, can be arranged in various layers 5, 6 of the measuring cell holder 3 so that for example an extension and compression of the measuring cell holder 3 can be detected. In the case of the first layer 5, for example the optical waveguide can be the core, and the second layer 6 can be an additional optical waveguide medium or the coating 7. As shown by way of example in FIG. 2, the pressure measuring device 1 comprises a measuring cell holder 3 having a plurality of layers 5, 6, wherein a layer 5 having FBG sensors 4 is in the form of an optical waveguide, and the additional layer 5 having piezoelectric sensors 4.1 can be in the form of an electric cable. The additional layer 6 can be for example a coating layer. The pressure measuring device 1 according to FIG. 2 additionally shows a protective layer 7.

It is also possible to produce measuring cell holders which comprise only one core region, to which measuring cells are then connected in turn, or in which measuring cells are arranged. Measuring cell holders of this type generally do not comprise a coating region. In the case of the cable, the first layer 6 can be a core region, in which the electric wires extend, and the second layer 6 can be a coating region of the cable. Further options for increasing the measuring sensitivity include for example thinning the optical waveguide by etching or by stretching at the fibre tip so that the fibres are in the form of microstructured fibres. As a result, not only is the measuring sensitivity increased, but the stiffness of the optical waveguide is also reduced.

Furthermore, the measuring cell holder 3 can comprise a biocompatible protective layer 7. In this case, said layer can be for example a plastics coating which is applied as mechanical protection to the surface of the measuring cell holder 3 and is designed to be biocompatible. The pressure measuring device can be used to measure pressure in spaces filled with liquid, in which for example hydrostatic pressure vibration amplitudes are measured. The FBG sensors 4 are located in the measuring cell holder 3 with a spacing of from 500 mm to 0 mm, preferably 100 mm to 3 mm, particularly preferably 8 mm to 4 mm, and have a length of approximately 1 mm to approximately 500 mm, preferably 2 mm to 200 mm, particularly preferably 3 mm to 20 mm. The optical waveguide is designed to be as flexible as possible so as to be able to follow the narrow and rigidly predefined conditions in a biological system.

FIG. 3 is a schematic view of a pressure measuring system in a biological system. It has surprisingly been found that commercially available telecommunications optical waveguides having a fibre diameter of 125 μm or even 80 μm can be used for the pressure measuring device 1 according to the invention. However, any other fibre diameters can also be used, such as heart-specific diameters of at most 0.36 mm.

The measuring cell holder 3 is connected at the first end 10, which is close to the evaluation unit, to a light source 14 and an optical sensor 15 via a coupler 12, a connector 13 or circulator (not shown). The evaluation, i.e. the calculation of the pressure, is carried out by means of a data processing unit 16. The activation of the FBG sensors 4 is carried out by light sources 14 which are conventional in the industry, such as adjustable narrow-band lasers or spectrally broadband, respectively fibre-coupled light sources. The evaluation is carried out by means of conventional optical sensors 15, depending on the light source 14 used, merely as a photosensor or as a system consisting of a light-frequency separator and a sensor, for example a monochromator and a charge-coupled device (CCD) line. The light source 14 and the sensor 15 are coupled in by means of conventional systems, such as an optical coupler 12 or circulator (not shown). The pressure measuring device 1 is connected to the signal system by means of a commercially available optical waveguide connector 13.

FIG. 4 is a schematic view of a pressure measuring device comprising a coating. At least one FBG sensor 4 is present as a reference measuring cell in an axially inflexible region 8 of the measuring cell holder 3. By introducing metal into the measuring cell holder 3 or by means of additional coatings, for example with X-ray contrast stripes, the location of the pressure measuring device can be determined using for example X-ray inspection. Spherical metal particles can also be shifted when extruding with the extruding substance. The metal particles can also be produced from a transition metal. Although said particles are detected during the X-ray, they do not generate any significantly disruptive interference during a nuclear magnetic resonance spectroscopy. Furthermore, a marker can be integrated in the measuring cell holder 3. The marker can be for example a transition metal, for example tantalum, so that it is possible to use the pressure measuring device in MRI, and imaging can take place in this case. The mentioned metal which is introduced can also be used in the form of splints, sleeves or meshes, optionally comprising rings at the ends, in order to give the pressure measuring device greater stiffness in places and thus protect the pressure measurements against artefacts as a result of bending, tensile, compressive or shearing forces in the pressure measuring device. This can also be used in the case of reference measuring cells, around which for example a sleeve or splinting is arranged, so that only the temperature in the biological system, and not the extension of the measuring cell holder, exerts an effect on the properties of the FBG sensors.

FIG. 5 shows an example of an application for measuring epidural pressure. A pressure is to be detected in order to diagnose a central lumbar spinal stenosis, wherein topographical epidural pressure relief is carried out. The pressure measuring device 1 is introduced up to approximately a meter deep into the spinal canal via an epidural needle 17 of a few centimeters, preferably through the ligamentum flavum 20 which is located between the spinous processes 19 of the lumbar spine. Pressures of from 1 up to at least 150 mmHg can be detected on a measuring portion of from 1 to 30 cm, wherein the FBG sensors 4 are present with a spacing of approximately 1 cm in a measuring cell holder 3 which is approximately 0.6 mm thick and approximately 50 cm long, with an adjoining 5 meter-long cable. The pressure measuring device 1 can comprise markers 8, for example made of tantalum, at the second end 11 which is remote from the evaluation unit and in an additional position on the measuring cell holder 3. As a result, the pressure measuring device can be made visible in an X-ray image converter, in CT or MRI.

A prepared presentation of the derived values in relation to a loaded, scaled image of the lumbar spine means that both static and dynamic individual measurements and time curves can be documented. The pressure measuring device 1 comprises working channels (not shown) which can be provided via corresponding outputs such as 18 with small lumina for applying medicines. A software obtains continuous or intermittent measuring data, for example at 50 Hz per measuring cell, about each pressure state in the pressure measuring device 1 and thus makes it possible to draw conclusions regarding the pressure ratios relative to the location of the pressure measuring device 1. By means of a native X-ray, a CT or MRI, an absolute determination of the location of the pressure measuring device can additionally be carried out.

Using the pressure measuring device, it is possible to continuously record the epidural pressure waves in sync with breathing or the pulse, above, at the height of and/or below the maximum spinal stenosis, for example as an intraoperative monitoring of the decompression of the dural sac. On the basis of the amplitude of the pressure waves, preoperative and intraoperative indications or indication examinations can be established taking into account neighbouring segments which are adjacent to the maximum stenosis, i.e. expanding the decompression. Furthermore, surprisingly, clinically relevant narrow points can be established by determining the difference in the amplitudes above the basic pressure.

By means of the pressure measuring device, dynamic and static pressure measurements can be carried out using measurements under a standard position/standard movement schedule, for example lying, sitting (bending forwards/backwards), standing (bending forwards/backwards), lying down/standing up, sitting down/standing up, climbing stairs, treadmill test with a specific location of the pressure measuring device and recording using for example a mobile device or radio transmission of the data.

FIG. 6 shows a pressure measuring device comprising a protective envelope and an atraumatic tip, and FIG. 7 is a sectional view of a pressure measuring device comprising a stiffening means. The pressure measuring device 1 can consist of a plurality of measuring cell holders 3, which are surrounded by a protective layer or protective envelope 7 made of for example plastics material. At the end 11 which is remote from the evaluation unit 11, an atraumatic tip 2 is arranged. The atraumatic tip 22 is produced from a plastics material of a type such that the biological system is not injured when the pressure measuring device 1 is introduced and guided through. A sectional view of a pressure measuring device 1 comprising a protective envelope 7 is shown in FIG. 7, and a sectional view of a pressure measuring device comprising three measuring cell holders is shown in FIG. 12. A stiffening means 21 is arranged in the centre of the protective envelope 7. In this case, the stiffening means can be for example a wire-shaped means which is produced from aromatic polyamides. The stiffening means 21 can also be designed to be web-shaped. A web made of the previously mentioned plastics materials lends itself in particular to this case. A plurality of measuring cell holders 3 can be present in the pressure measuring device 1, in particular in the protective envelope 7. For example, three measuring cell holders 3 can be arranged around a working channel 9, wherein it is also possible to arrange two or more than three measuring cell holders 3 in one of the layers of the pressure measuring device. The second layer 6 can be designed for example as a coating region.

FIG. 8 shows an arrangement of a plurality of measuring cell holders in a protective envelope. The measuring cell holders 3 are arranged eccentrically and so as to be offset from one another in each case by 1/n, for example in the case of three measuring cell holders, ⅓ of the pitch 24 of the FBG sensors 4. This makes it possible to detect, separate and evaluate changes in the reflection wavelength, as a result of bends, extensions and radial forces, of the FBG sensors 4 with better spatial resolution, as offered only by the pitch 24 of the FBG sensors 4. There are also no measurement-free points between the FBG sensors 4 due to the overlapping of the fields. The offset with which the FBG sensors 4 are arranged relative to one another is equal to 1/n of the pitch 24, wherein n is the number of measuring cell holders 3 in the pressure measuring device, in particular in the protective envelope 7. FIG. 8 shows an embodiment comprising three measuring cell holders 3, and therefore n=3, and the offset is equal to a third of the pitch (the distance from the centre of an FBG sensor field to the centre of the next) (indicated by the dashed lines). However, it is also possible for only two measuring cell holders 3, i.e. optical waveguides, to be arranged in a protective envelope 7, for example a casing, around a working channel. More than three measuring cell holders 3 are also possible. As a result, it is possible to carry out a duration measurement, and interferences, such as the effect of temperature on the FBG sensors, can be compensated. In addition, in the working channel arranged between the measuring cell holders 3, a stiffening or guide means can be introduced, by means of which the stiffness of the pressure measuring device can be adapted to each use of the pressure measuring device by using stiffening or guide means having different stiffness.

FIG. 9, FIG. 10 and FIG. 11 show views of a Fabry-Pérot interferometer in a, for example atraumatic, tip. FIG. 9 shows the cross section of a pressure measuring device 1 comprising a measuring cell holder 3 and a protective envelope. In this case, it should be the end which is remote from the evaluation unit comprising an atraumatic tip. The sectional view (A-A) with the Fabry-Pérot interferometer 23 which is present in the tip 22 can be seen in FIG. 10, and a schematic side view thereof in FIG. 11. In the tip 22, there is a Fabry-Pérot interferometer 23, which was produced for example in MEMS technology, which interferometer is composed of at least one end of a measuring cell holder, in particular of an optical waveguide 3 (end which is remote from the evaluation unit 11) and a mirrored membrane 24 which can be deformed by the effect of pressure and consequent deformation of the tip 22.

Said Fabry-Pérot interferometer 23 forms a pressure sensor which can be evaluated for example in the same wavelength window as the FBG sensors. FIG. 11 shows the general functional principle of a Fabry-Pérot interferometer 23. At the optical waveguide end 11, two partially reflective mirrors 25 are arranged, which reflect light beams (R1 and R2). Between the mirrors 25 is a distance I. The transmission spectrum of said arrangement exhibits narrow transmission maxima for wavelengths, which meet the resonance conditions, whilst other spectral ranges in the transmission are almost completely eliminated. This takes place by means of constructive or destructive interference of the partial beams. As a result of the fact that the mirrored membrane 24 is designed to be deformable, an acting force (pressure) brings about a change in the transmission spectrum and consequently of the reflected beams, so that even low changes in pressure at the tip 22 can be measured. This is particularly advantageous when introducing the pressure measuring device 1 into a biological system and when guiding the pressure measuring device 1 through said system, and in order to calibrate the pressure measuring device to temperature artefacts and to measure other pressure ranges and other pressure resolutions, optionally also in other measuring frequencies.

The invention claimed is:

1. Pressure measuring device for measuring pressure in a biological system, comprising a flexibly or resiliently designed measuring cell holder with at least one optical waveguide,
   wherein the measuring cell holder has a first end which is close to an evaluation unit,
   wherein the measuring cell holder has a second end which is remote from the evaluation unit,
   wherein, in the measuring cell holder, there are at least two fiber Bragg grating sensors which are arranged at a distance from one another,
   wherein the pressure measuring device further comprises a Fabry-Pérot interferometer,
   wherein the Fabry-Perot interferometer comprises the second end of the measuring cell holder and comprises a mirrored deformable membrane, and
   wherein the Fabry-Perot interferometer forms a pressure sensor able to be evaluated in the same wavelength window as the at least two fiber Bragg grating sensors.

2. Pressure measuring device according to claim 1, wherein the measuring cell holder comprises at least two layers, and the fiber Bragg grating sensors are arranged in a first and/or second layer.

3. Pressure measuring device according to claim 1, wherein the measuring cell holder comprises an outer protective layer which comprises a biocompatible material.

4. Pressure measuring device according to claim 1, wherein the optical waveguide is a polymer optical fiber or a glass fiber.

5. Pressure measuring device according to claim 1, wherein the measuring cell holder comprises at least two layers and a piezoelectric sensor in a first and/or second layer.

6. Pressure measuring device according to claim 1, wherein a plurality of fiber Bragg grating sensors which are present in the measuring cell holder have different resonance properties.

7. Pressure measuring device according to claim 1, wherein at least one fiber Bragg grating sensor is present in an axially inflexible region of the measuring cell holder as a reference measuring cell.

8. Pressure measuring device according to claim 1, wherein the measuring cell holder comprises at least one marker made of a metal or transition metal which is present in or on a layer of the measuring cell holder.

9. Pressure measuring device according to claim 1, wherein the measuring cell holder comprises at least one working channel having an input and an output.

10. Pressure measuring device according to claim 1, wherein an atraumatic tip or guiding structure is present at the second end.

11. Pressure measuring device according to claim 1, wherein the measuring cell holder is connected at the first end to a light source and an optical sensor by a coupler, a connector or circulator.

12. Pressure measuring device according to claim 1, wherein at least two measuring cell holders are arranged in a protective layer which comprises a biocompatible material.

13. Pressure measuring device according to claim 1, wherein at least two measuring cell holders are arranged in the longitudinal direction of a protective layer so as to be offset from one another.

14. Pressure measuring device according to claim 1, wherein at least two measuring cell holders are arranged so as to be offset from one another by 1/n of a pitch of an FBG sensor, and n is the number of the measuring cell holders in a protective layer.

15. Pressure measuring device according to claim 1, wherein the pressure measuring device comprises a stiffening device.

16. Method for measuring a pressure in a biological system, the method comprising steps of:
   introducing a radially flexible measuring cell holder with at least one optical waveguide having a first end and a second end into the biological system, the measuring cell holder having a Fabry-Perot interferometer and having at least two fiber Bragg grating sensors arranged at a distance from one another, the first end being close to an evaluation unit and the second end being remote from the evaluation unit, the Fabry-Perot interferometer comprising the second end of the measuring cell holder and comprising a mirrored deformable membrane, the Fabry-Perot interferometer forming a pressure sensor able to be evaluated in the same wavelength window as the at least two fiber Bragg grating sensors,
   measuring via the Fabry-Perot interferometer a pressure in the biological system as the measuring cell holder is introduced into the biological system,
   positioning the measuring cell holder at a first measuring point in the biological system,
   capturing via a first Bragg grating sensor of the at least two fiber Bragg grating sensors a first measurement result at the first measuring point,
   capturing via the first Bragg grating sensor or via a second Bragg grating sensor of the at least two fiber Bragg grating sensors a second measurement result, and
   capturing a measurement distance.

17. Method according to claim 16, wherein the second measurement result is captured at a measuring point which is at a distance from the first measuring point.

18. Method according to claim 16, wherein the second measurement result is captured at the first measuring point at a later time than the first measurement result.

* * * * *